US00PP26592P2

(12) United States Plant Patent
Deng et al.

(10) Patent No.: US PP26,592 P2
(45) Date of Patent: Apr. 5, 2016

(54) ***CALADIUM* PLANT NAMED 'PASSIONISTA'**

(50) Latin Name: *Caladium×hortulanum*
Varietal Denomination: Passionista

(71) Applicant: Florida Foundation Seed Producers, Inc., Marianna, FL (US)

(72) Inventors: Zhanao Deng, Riverview, FL (US); Brent K. Harbaugh, Bradenton, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 14/756,219

(22) Filed: Aug. 18, 2015

(51) Int. Cl.
*A01H 5/12* (2006.01)

(52) U.S. Cl.
USPC ..... Plt./373

(58) Field of Classification Search
USPC ..... Plt./373
See application file for complete search history.

*Primary Examiner* — Keith Robinson
(74) *Attorney, Agent, or Firm* — Christopher & Weisberg, P.A.

(57) ABSTRACT

A new and distinct cultivar of *Caladium* plant named 'Passionista', characterized by its mounding growth habit, elongated leaves that have a large pink center, pink primary veins, netted pink secondary veins, and mottled margins, and plants that are attractive in containers and shady landscapes.

3 Drawing Sheets

ACKNOWLEDGEMENT OF FEDERAL RESEARCH SUPPORT

This invention was made with government support under FLA-BRA-04162 awarded by the Cooperative State Research, Education, and Extension Service, USDA and under FLA-GCR-005065 awarded by the National Institute of Food and Agriculture, USDA. The government has certain rights in the invention.

Genus and species: *Caladium×hortulanum.*
Cultivar denomination: 'Passionista'.

CROSS-REFERENCE TO RELATED APPLICATION n/a

BACKGROUND OF THE NEW CULTIVAR

The present invention relates to a new and distinct cultivar of *caladium* plant, botanically known as *Caladium×hortulanum*, commercially referred to as a strap leaf-type or lance leaf-type *caladium* and hereinafter referred to by the name 'Passionista'.

*Caladiums* (also referred to as *Caladium* plants) are ornamental aroids frequently used as pot and landscape plants for their colorful foliage and ease of growing. The objective of the Inventors' breeding program is to create new *Caladium* cultivars that have compact growth habit, numerous leaves, attractive foliage, and exceptional container and landscape performance.

The new *Caladium* cultivar 'Passionista' originated from a cross between 'Aaron' (commercial cultivar, not patented) and 'Florida Red Ruffles' (U.S. Plant Pat. No. 13,136) that was made in Bradenton, Fla. in spring 2004. The new *Caladium* cultivar 'Passionista' was discovered and selected by the inventors as a single plant in Florida in August 2005. The *Caladium* cultivar 'Passionista' has been found to retain its distinctive characteristics through at least nine generations of successive asexual propagations conducted in Wimauma, Fla. via tuber divisions since April of 2006.

Plant Breeder's Rights for this cultivar have not been applied for. 'Passionista' has not been made publicly available more than one year prior to the filing of this application.

SUMMARY OF THE INVENTION

The new *Caladium* cultivar has not been observed under all possible environmental conditions. The phenotype may vary somewhat with variations in environment such as temperature, light intensity, water status, fertilizer rate and type, without, however, any variance in genotype.

The following are the most outstanding and distinguishing characteristics of this new *Caladium* cultivar when grown under (normal or standard) horticultural practices in Wimauma, Fla. The combination of these characteristics distinguishes 'Passionista' as a new and distinct cultivar of *Caladium:*

1. Symmetrical, outwardly arching plant form;
2. Mounding, moderately dense growth habit;
3. Elongated ovate leaves that have a large pink center, pink mid and primary veins, netted pink secondary veins throughout the leaf, and mottled margins.
4. Attractive plants in containers and shady landscapes.

The new *Caladium* cultivar 'Passionista' differs from its female parent, 'Aaron' in the following characteristics:

1. Plants of 'Passionista' are shorter than plants of 'Aaron';
2. Leaves of 'Passionista' are elongated, with no or only small, separated lobes, and the petioles are attached to the base of leaves. Whereas leaves of 'Aaron' are heart-shaped, with two large lobes that are partially joined, and the petioles are attached to the back of the leaves;
3. Leaves of 'Passionista' are narrower than the leaves of 'Aaron'; and 4. Leaves of 'Passionista' have a large pink center, pink mid veins and primary veins, and netted pink secondary veins, whereas leaves of 'Aaron' have a white center and white veins.

The new *Caladium* cultivar 'Passionista' differs from its male parent, 'Florida Red Ruffles', in the following characteristics:

1. Plants of 'Passionista' are taller and more spreading than plants of 'Florida Red Ruffles';
2. Leaves of 'Passionista' have a pink center and pink veins, whereas leaves of 'Florida Red Ruffles' have a dark red center and dark red veins;
3. Leaf margins of 'Passionista' are green with white mottling, whereas margins of 'Florida Red Ruffles' are solid green;
4. Petioles of 'Passionista' are green, whereas petioles of 'Florida Red Ruffles' are dark black or pinkish in color; and
5. Leaves of 'Passionista' tend to be bleached out by full sun, whereas leaves of 'Florida Red Ruffles' tend to become glossy.

DESCRIPTION OF THE FIGURES

The accompanying photographs (as shown in FIGS. 1-3) illustrate the overall appearance of the new *Caladium* cultivar. These photographs show the colors as true as can be reasonably obtained in colored reproductions of this type. Colors in the photographs may differ slightly from the color values cited in the detailed botanical description, which accurately describe the colors of the new *Caladium* cultivar.

DETAILED BOTANICAL DESCRIPTION

Figure 1:
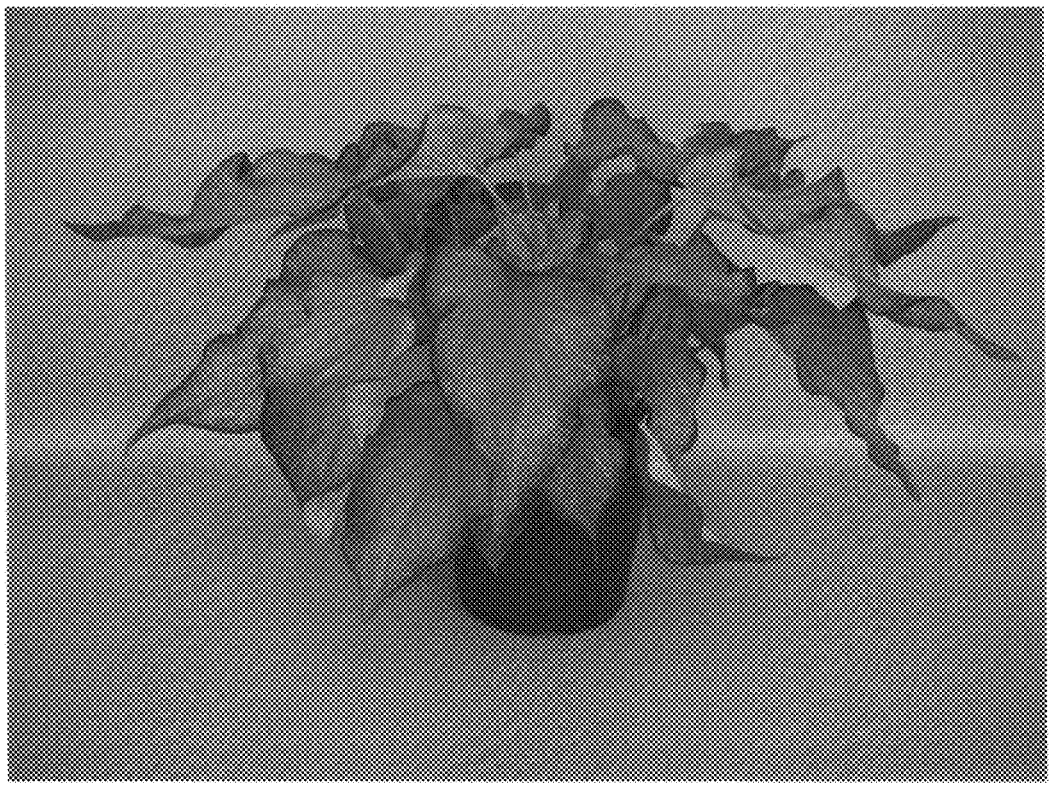
FIG. 1 shows a photograph of a side view of a typical plant of 'Passionista' grown in a 20-cm diameter container in a shadehouse.
Figure 2:
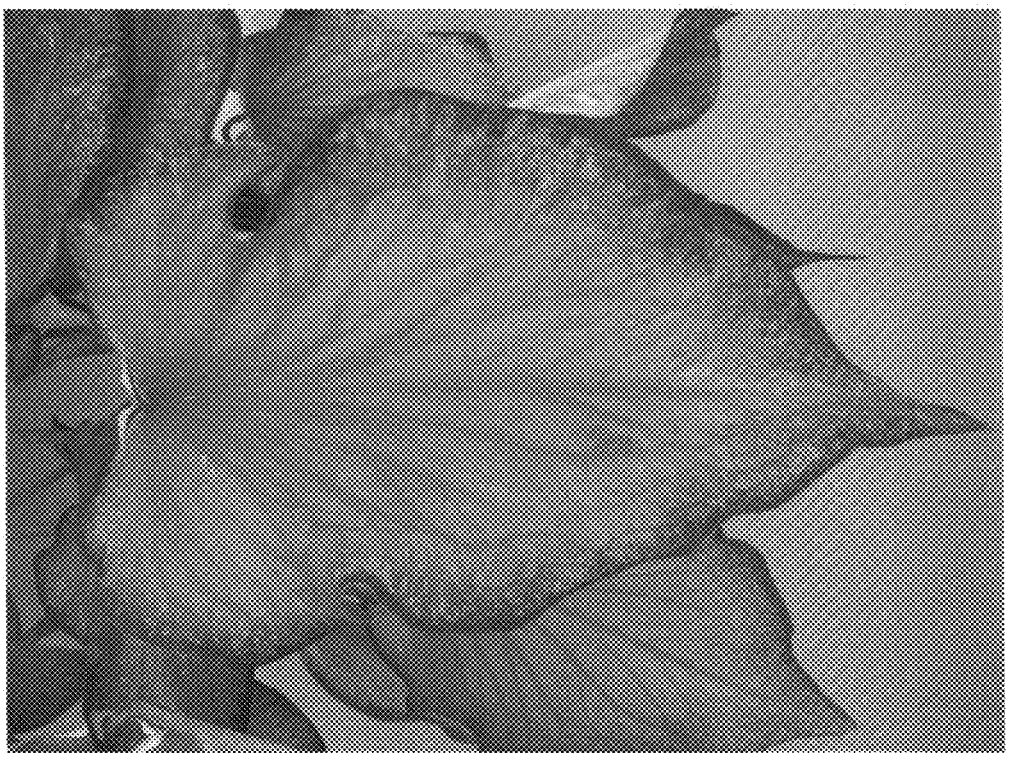
FIG. 2 shows a photograph of a top view of a typical leaf of 'Passionista' grown in a 20-cm diameter container in a shadehouse.
Figure 3:
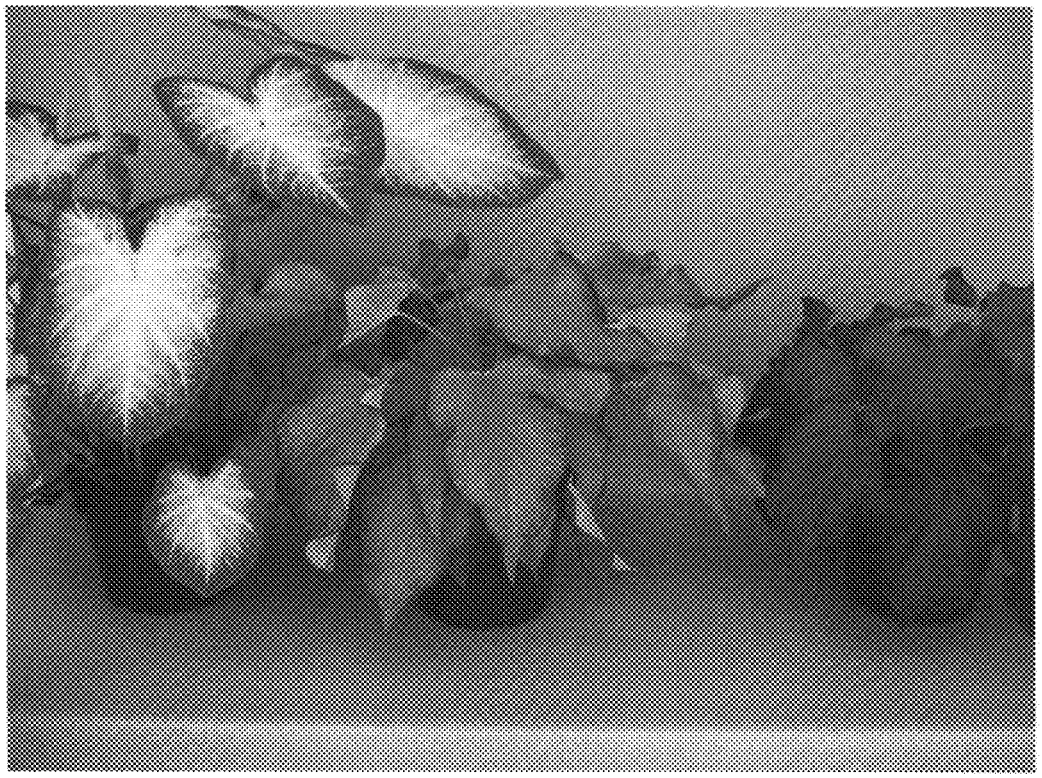
FIG. 3 shows a photograph of a side view of typical plants of 'Aaron (left), 'Passionista' (center), and 'Florida Red Ruffle' (right) grown in 20-cm diameter container in a shadehouse.

In the following description, color references are made to The Royal Horticultural Society (R.H.S.) Colour Chart, 1986 Edition, except where general terms of ordinary dictionary significance are used. The features of 'Passionista' described herein are shown in FIGS. 1-3.

Description of Growing Conditions

The following observations and measurements describe plants grown in 20.3-cm containers in Wimauma, Fla., during the summer in a polypropylene-covered shadehouse. All plants were grown under conditions and practices similar to those generally used in commercial *Caladium* production.

During the production of the plants, day temperatures ranged from approximately 23.5° C. to 34.4° C., night temperatures ranged from approximately 20.5° C. to 23.5° C., and light levels were approximately 944 foot-candles in the shadehouse. Plants grown in the shadehouse were approximately seven weeks from planting tubers when the photographs and the detailed description were taken. Plants grown in the outdoor nursery were approximately three months from planting No.1-sized tubers when the detailed description was taken.

Botanical Description

Botanical classification:

*Family*.—Araceae.

*Botanical name*.—*Caladium×hortulanum*.

*Common name*.—*Caladium*.

*Cultivar*.—'Passionista' (*Caladium×hortulanum* cultivar Passionista).

Parentage:

*Female or seed parent*.—'Aaron', not patented.

*Male or pollen parent*.—'Florida Red Ruffles' (U.S. Plant Pat. No. 13,136).

Propagation:

*Type*.—By tubers and by tuber divisions.

*Time to initiate roots, summer*.—Approximately seven to ten days at 32° C.

*Time to initiate roots, winter*.—Approximately two to three weeks at 24° C.

Tuber description: Jumbo-sized (6.4 to 8.9 cm in diameter) tubers are multi-segmented, bearing six to nine dominant buds.

*Height of tubers*.—About: 2.5 cm.

*Diameter of tubers*.—About 7 cm.

*Texture*.—Thick, starchy inside; slightly brittle between tuber branches.

*Color*.—Epidermis, Close to brown (RHS 200B); Interior, yellow (RHS 7A).

*Root description*.—Dense, thick and yellow-white (RHS 159D) fleshy roots.

Plant description:

*Type*.—Herbaceous perennial.

*Plant form*.—Semi-upright, outwardly arching and symmetrical plant.

*Growth habit*.—Compact and mounding, moderately dense foliage, suitable for containers 10.0 cm or larger in diameter. Leaf petioles arising from tubers; petioles mostly semi-upright and curving outwardly with development.

*Plant height, from soil level to top of leaf plane, shadehouse-grown plants*.—Approximately 33 cm.

*Plant spread, shadehouse-grown plants*.—Approximately 76 cm×64 cm.

*Plant spread, outdoor nursery-grown plants*.—Approximately 46 cm×43 cm.

Foliage description (shadehouse-grown and outdoor nursery-grown):

*Length, shadehouse-grown plants*.—Approximately 24 cm.

*Width, shadehouse-grown plants* (*flattened*).—Approximately 15.7 cm.

*Length, outdoor nursery-grown plants*.—Approximately 14 cm.

*Width, outdoor nursery-grown plants* (*flattened*).—Approximately 7.6 cm.

*Shape*.—Ovate.

*Apex*.—Acuminate to acute.

*Base*.—Cordate.

*Margin*.—Entire, slightly undulate.

*Texture, upper surface*.—Smooth, glabrous.

*Texture, lower surface*.—Smooth, glabrous, glaucous.

*Venation pattern*.—Pinnate.

Leaf color, shadehouse-grown plants:

*Developing and fully expanded leaves*.—Upper surface: Center: Close to red (RHS 54B). Border and margins: Close to green (RHS 139A), with speckling. of white (RHS 155B). Basal notch: None. Venation: Midrib: Close to red (RHS 53C). Primary and netted veins: Close to red (RHS 53C). Lower surface: Center: Close to greyed-purple (RHS 185D). Border and margins: Close to greyed-green (RHS 191A), with speckling of greyed-yellow (RHS 162D). Venation: Midrib: Close to greyed-purple (RHS 184D). Primary: Close to greyed-purple (RHS 185D).

Leaf color, outdoor nursery-grown plants:

*Developing leaves*.—Upper surface: Center: Close to red-purple (RHS 60B). Border and margins: Close to green (RHS 137A), with mottling. Venation: Midrib: Close to red (RHS 53B). Primary: Close to greyed-purple (RHS 185A). Lower surface: Center: Close to greyed-purple (RHS 184C). Border and margins: Close to greyed-green (RHS 191A), with mottling of yellow-white (RHS 158B). Venation: Midrib: Close to greyed-orange (RHS 177C). Primary: Close to greyed-brown (RHS 199C and 199D).

*Fully expanded leaves*.—Upper Surface: Center: Close to red (RHS 51A and 51B). Border and margins: Close to green (RHS 137A), with mottling of yellow-white (RHS 158B) toward the center. Venation: Midrib: Close to red (RHS 53C). Primary: Close to greyed-purple (RHS 185B). Lower surface: Center: Close to greyed-purple (RHS 184D), with mottling of yellow-white (RHS 158C). Border and margins: Close to greyed-green (RHS 191A), with mottling of yellow-white (RHS 158B). Venation: Midrib: Close to greyed-red (RHS 179C and 179D). Primary: Close to green (RHS 143B and 143C).

Petioles:

*Aspect*.—Mostly erect, curving outwardly with development, attached to the base.

*Length, shadehouse-grown plants*.—Approximately 19 to 27 cm.

*Diameter, distal, shadehouse-grown plants*.—Approximately 4.6 mm.

*Diameter, proximal, shadehouse-grown plants*.—Approximately 6.8 mm.

*Length, outdoor nursery-grown plants*.—Approximately 14.0 cm to 17.0 cm.

*Diameter, distal, outdoor nursery-grown plants*.—Approximately 3.2 mm.

*Diameter, proximal, outdoor nursery-grown plants*.—Approximately 4.5 mm.

*Strength*.—Strong; flexible.

*Color, shadehouse-grown plants*.—Close to greyed-red (RHS 179D), with speckles of greyed-green (RHS 189A), close to yellow-green (RHS 148A), or yellow-green (RHS 146B).

*Color, outdoor nursery-grown plants*.—Close to brown (RHS 200D), with streaks of brown (RHS 200C), or older petioles, distal, greyed-brown (RHS 199A) proximal, green (RHS 137A).

*Wing length, shadehouse-grown plants*.—Approximately 4.3 cm to 7.0 cm.

*Wing diameter, shadehouse-grown plants*.—Approximately 5.4 mm to 8.9 mm.

*Wing length, outdoor nursery-grown plants*.—Approximately 4.5 cm to 6.5 cm.

*Wing diameter, outdoor nursery-grown plants*.—Approximately 4.7 mm to 7.5 mm.

*Wing color, shadehouse-grown plants*.—Close to white (RHS 155C), with speckles of brown (RHS 200D).

*Wing color, outdoor nursery-grown plants*.—Close to greyed-green (RHS 196D), with dashes of yellow-green (RHS 147A or 147B).

Inflorescence description:

*Inflorescence arrangement*.—Upright hooded spathes surrounding a columnar spadix borne on an upright scape. Spadix carries sessile, simple female and male flowers separated into two zones. Female flowers arranged on the lower one-third of the spadix; male flowers arranged on the upper two-thirds of the spadix. Sterile flowers develop between female and male flower zones. Spadix constricts near the sterile flower zone.

*Fragrance*.—None detected.

*Natural flowering season/longevity*.—Plants of 'Passionista' typically flower during spring or early summer in central Florida. Flowers develop about seven weeks after growth commence. Inflorescences last about four days before fading.

*Spathe*.—Length: Approximately 11.7 cm. Width: Distal: Approximately 2.7 cm. Proximal: Approximately 2.1 cm. Shape: Ovate to somewhat obovate. Apex: Acute to acuminate. Base: Tapering. Margin: Entire. Texture: Upper and lower surfaces: Smooth, glabrous. Color: Front surface: Upper two-thirds: Close to white (RHS 155A). Lower one-third: Close to green (RHS 137D) with streaks of green (RHS 138D). Rear surface: Upper two-thirds: Close to yellow-white (RHS 158C) with streaks of yellow-green (RHS 145D). Lower one-third: Close to green (RHS 137D) with streaks of green (RHS 138DC) with some bands of greyed-purple (RHS 185D) at the base.

*Spadix*.—Length, entire spadix: Approximately 8.2 cm. Length, male flower zone: Approximately 4.6 cm. Length, sterile flower zone: Approximately 1.7 cm. Length, female flower zone: Approximately 1.8 cm. Diameter, male flower zone: Approximately 8.2 mm. Diameter, sterile flower zone: Approximately 7.1 mm. Diameter, female flower zone: Approximately 8.9 mm. Shape: Spindle-shaped to columnar. Apex: Obtuse. Base: Obtuse. Aspect: Upright. Color, mature, male zone: Close to yellow-white (RHS 158A). Color, mature, sterile zone: Close to yellow (RHS 155D). Color, mature, female zone: Close to yellow-orange (RHS 20C). Male flowers: Quantity per spadix: Approximately 124. Shape: Obovate. Height: Approximately 3.6 mm. Diameter: Approximately 3.2 mm. Pollen color: Close to yellow (RHS 10B). Amount of pollen: Scant. Female flowers: Quantity per spadix: Approximately 133. Shape: Obovate. Height: Approximately 1.7 mm. Diameter: Approximately 1.5 mm.

*Scape*.—Length: Approximately 17 cm. Diameter: Approximately 6.3 mm. Strength: Sturdy, flexible. Aspect: Erect, but some curving outward. Texture: Smooth, glabrous, glaucous. Color: Close to yellow-green (RHS 146B), or others with greyed-red (RHS 179C) with streaks of brown (RHS 200D). Just below spathe: Close to yellow-green (RHS146D).

*Seed and fruit*.—Seed and fruit development has not been observed on inflorescences that were not hand-pollinated.

Disease/pest resistance: Plants of 'Passionista' have been observed to be somewhat resistant to *Xanthomonas* leaf spot.

Temperature tolerance: Tolerant to temperatures ranging from approximately 7° C. to approximately 40° C.

Sunburn tolerance: Leaf colors tend to fade under high light levels.

Comparison with Known Cultivars

'Passionista' was evaluated for tuber production at the Gulf Coast Research and Education Center in Wimauma, Fla. in 2007, 2008, and 2009. The soil was EauGallie fine sand with about 1% organic matter and a pH value between 6.2 and 7.4. *Caladium* plants were grown in the field using a plastic-mulched raised-bed system. For the 2007 evaluation, ground beds (81 cm wide, 20 cm high) were fumigated on 3 April with a mixture of 67% methyl bromide and 33% chloropicrin (by volume) at the rate of 196 $kg \cdot ha^{-1}$. *Caladium* seed pieces (tuber pieces, approximately 2.5×2.5×2.5 cm) were planted manually on 26 April with approximately 25.4 cm between-row spacing and approximately 15.2 cm in-row spacing. Drip tapes were buried under the plastic mulch and delivered approximately 6 mm of water to the bed per day. Fertigation (through the drip irrigation system) began when young *caladium* plants emerged from the soil, supplying soluble fertilizer (6N-0.8P-3.9K) at the rate of approximately 1.9 kg of $nitrogen \cdot ha^{-1} \cdot day^{-1}$ and a total 290 kg of $nitrogen \cdot ha^{-1}$ per growing season. Tubers (new crop) were dug, washed, and dried in early January 2008. Dried tubers from each experimental field plot were weighed, graded, and counted in late January 2008. Tuber grading was by the tuber maximum diameter: Super Mammoth (greater than 11.4 cm), Mammoth (8.9 to 11.4 cm), Jumbo (6.4 to 8.9 cm), No.1 (3.8 to 6.4 cm), and No. 2 (2.5 to 3.8 cm). Tuber grades and counts were converted into a Production Index (PI) to show the relative economic value of the harvested tubers per field plot: PI=8n (Supper Mammoth)+6n (Mammoth)+4n (Jumbo)+2n (No.1)+1n (No.2), where n=number of tubers in the grade. The relative values assigned to the five tuber grades in calculating PIs were based on the relative market prices provided by Florida *caladium* tuber producers.

For the 2008 evaluation, beds were fumigated with a mixture of 80% methyl bromide and 20% chloropicrin (by volume) at the rate of 448 $kg \cdot ha^{-1}$. *Caladium* seed pieces were planted on 18 Apr. 2008 at approximately 15-cm spacing between and within rows. The irrigation and fertigation system was the same as the one used in 2007. Tubers were dug from 2 to 8 Dec. 2009, followed by washing, drying, weighing, grading, and counting as done in 2007.

For the 2009 evaluation, beds were fumigated on 27 February with a mixture of 50% methyl bromide and 50% chloropicrin (by volume) at the rate of 196 $kg \cdot ha^{-1}$. *Caladium* seed pieces were planted on 9 Apr. 2009 at approximately 15-cm spacing between rows and in rows. The irrigation and fertigation system was the same as the one used in 2007, but one teaspoon (approximately seven grams) of OSMOCOTE® controlled-release fertilizer (15N-2.6P-10K, 5-6 months) was applied to each plant on 21 July. Tubers were dug from 30 Nov. to 2 Dec. 2009, followed by washing, drying, weighing, grading, and counting as was done in 2007.

Field plots were arranged each season in three randomized complete blocks, and each plot (1.2 $m^2$) was planted with 30 *caladium* seed pieces. Two commercial cultivars 'Florida Red Ruffles' and 'Florida Sweetheart' were included in each block. Analyses of variance were conducted using the PROC GLM procedure in SAS (SAS Institute, Cary, N.C.) to compare the tuber yields of 'Passionista' to that of 'Florida Red Ruffles' and 'Florida Sweetheart' (U.S. Plant Pat. No. 8,526, now expired).

Table 1 shows the tuber weight, marketable tubers, production index, and grade distribution of 'Passionista' grown in Wimauma, Fla. in 2007, 2008, and 2009. Values presented for each year are means of three plots in three randomized complete blocks.

TABLE 1

| | Tuber | | |
|---|---|---|---|
| Cultivars | Weight (kg) | Marketable (no.) | Production index[z] |
| | Year 2007 | | |
| 'Passionista' | 4.3 a | $58.9^{NS}$ | $136.0^{NS}$ |
| 'Florida Red Ruffles' | 2.7 b | 42.2 | 84.4 |
| 'Florida Sweetheart' | 3.3 ab | 45.6 | 104.9 |
| | Year 2008 | | |
| Passionista' | 4.4 a | $66.1^{NS}$ | 184.5 a |
| 'Florida Red Ruffles' | 1.5 b | 50.1 | 81.1 b |
| 'Florida Sweetheart' | 1.9 b | 53.3 | 88.0 b |
| | Year 2009 | | |
| 'Passionista' | 2.9 a | 29.3 b | 81.0 a |
| 'Florida Red Ruffles' | 0.9 b | 24.7 b | 38.0 b |
| 'Florida Sweetheart' | 2.7 a | 47.0 a | 94.7 a |

| | Tuber grade distribution (%) | | | | |
|---|---|---|---|---|---|
| Cultivars | Super Mammoth | Mammoth | Jumbo | No. 1 | No. 2 |
| | Year 2007 | | | | |
| 'Passionista' | — | $7.6^{NS}$ | $18.3^{NS}$ | 43.3 e | $30.8^{NS}$ |
| 'Florida Red Ruffles' | — | 1.0 | 20.0 | 41.0 a | 37.9 |
| 'Florida Sweetheart' | — | 2.6 | 28.6 | 31.3 b | 37.5 |
| | Year 2008 | | | | |
| Passionista' | — | 4.3 a | 41.4 a | $36.9^{NS}$ | 17.4 b |
| 'Florida Red Ruffles' | — | 0 b | 3.9 c | 51.5 | 44.6 a |
| 'Florida Sweetheart' | — | 0 b | 17.4 b | 64.9 | 17.8 b |
| | Year 2009 | | | | |
| 'Passionista' | — | 6.9 a | 27.2 a | $52.1^{NS}$ | 12.7 c |
| 'Florida Red Ruffles' | — | 0.0 b | 4.4 b | 32.4 | 63.2 a |
| 'Florida Sweetheart' | — | 1.3 b | 19.5 ab | 38.9 | 40.3 b |

[z]The production index is an indicator of economic value of the crop harvested and is calculated as: N (No.2s) + 2N (No. 1s) + 4N (Jumbos) + 6N (Mammoth) + 8N (Super Mammoth); where N = number of tubers in each grade. Tubers graded by maximum diameter; No. 2 (2.5 to 3.8 cm), No. 1 (3.8 to 6.4 cm), Jumbo (6.4 to 8.9 cm), Mammoth (8.9 to 11.4 cm), and Super Mammoth (>11.4 cm).

Mean values with the same letters within columns are not significantly different at $P \leq 0.05$.

NS: not significantly different at $P \leq 0.05$.

As shown in Table 1, there were no significant differences between 'Passionista' and 'Florida Sweetheart' in tuber weight (4.3 kg and 3.3 kg), number of marketable tubers (58.9 and 45.6), and PI (136.0 and 104.9) in the 2007 growing season. Whereas in the 2008 growing season, 'Passionista' had a greater tuber weight (4.4 kg vs. 1.9 kg) and a higher PI (184.5 vs. 88.0) than 'Florida Sweetheart.' In the 2009 growing season, 'Passionista' and 'Florida Sweetheart' had similar tuber weights (2.5 kg and 2.7 kg, respectively) and similar PIs (81.0 and 94.7, respectively), but 'Passionista' produced fewer marketable tubers (29.3 vs. 47.0) than 'Florida Sweetheart'.

As shown in Table 1, the tuber weights of 'Passionista' were 59.3% (2007), 193.3% (2008), and 222.2% (2009) greater than the tuber weights of 'Florida Red Ruffles' in corresponding years, and the PIs of 'Passionista' were 61.1% (2007), 127.5% (2008), and 113.2% higher than the PIs of 'Florida Red Ruffles' in corresponding years.

As shown in Table 1, 'Passionista' produced more tubers in larger-size categories (Mammoth or Jumbo) and fewer tubers in the small size category (No. 2) than both 'Florida Sweetheart' and 'Florida Red Ruffles'. Specifically, 'Passionista' produced more No.1-sized tubers (41.3% vs. 31.3%) than 'Florida Sweetheart' in 2007, and more Mammoth-sized (4.3% vs. 0) and Jumbo-sized tubers (41.4% vs. 17.4%) than 'Florida Sweetheart' in 2008. 'Passionista' produced more Mammoth-sized (6.9% vs. 1.3%) and fewer No.2-sized tubers (12.7% vs. 40.3%) than 'Florida Sweetheart' in 2009.

As shown in Table 1, 'Passionista' produced more Mammoth-sized (4.3% vs. 0), more Jumbo-sized (41.4% vs. 3.9%), but fewer No.2-sized (17.4% vs. 44.6%) tubers than 'Florida Red Ruffles' in 2008. 'Passionista' also produced more Mammoth-sized (6.9% vs. 0), more Jumbo-sized (27.2% vs. 4.4%), but fewer No.2-sized (12.7% vs. 63.2%) tubers in 2009.

Table 2 shows a comparison of the plant height, number of leaves, leaf length, and leaf width of 'Passionista' with 'Florida Sweetheart', and 'Florida Red Ruffles', approximately 4 months after planting tuber pieces (propagules, approximately 2.54 cm each side) in ground beds in full sun in 2007 and 2009. Values presented are means of data from three replications and three plants measured per plot per year over two years.

TABLE 2

| Cultivars | Plant height (cm) | Leaves (no.) | Leaf length[z] (cm) | Leaf width[y] (cm) |
|---|---|---|---|---|
| 'Passionista' | 26.3 a[x] | 35.4[NS] | 21.7 a | 11.1 b |
| 'Florida Red Ruffles' | 17.9 b | 27.7 | 16.9 c | 10.0 b |
| 'Florida Sweetheart' | 22.8 a | 28.7 | 19.4 b | 13.4 a |

[z]Leaf length was measured on the largest leaves along the longest line from the leaf lobe to the leaf tip.
[y]Leaf width was measured on the largest leaves across the widest middle part.
[x]Mean values with the same letters within columns are not significantly different at $P \leq 0.05$.
NS: not significantly different at $P \leq 0.05$.

As shown in Table 2, plants of 'Passionista' from tuber pieces and grown in full for 4 months had an average height of 26.3 cm, which was about 3.5 to 8.4 cm taller than plants of 'Florida Red Ruffles' or 'Florida Sweetheart'. Leaves of 'Passionista' had an average size of 21.7 cm by 11.1 cm. Leaves of 'Passionista' were approximately 4.7 cm longer than the leaves of 'Florida Red Ruffles', and approximately 2.3 cm longer but 2.3 cm narrower than the leaves of 'Florida Sweetheart'.

Table 3 shows the landscape performance of 'Passionista' with 'Florida Sweetheart', and 'Florida Red Ruffles' when planted in ground beds in full sun in 2007, 2008 and 2009. Values presented are means of three replications in each year.

Landscape performance was evaluated on the same plots used for evaluating tuber production. A scale of 1 to 5 was used with 1 being very poor (few leaves and lack of vigor), and 5 being excellent (full plants, numerous leaves, and bright color display). A total of nine evaluations were conducted for plant performance over three growing seasons in July, August, and September 2007, August, September, and October 2008, and August, September, and October 2009.

TABLE 3

| | 2007 | | |
|---|---|---|---|
| Cultivars | July | August | September |
| 'Passionista' | 3.9[Z, NS] | 3.9[NS] | 2.9[NS] |
| 'Florida Red Ruffles' | 3.8 | 3.1 | 2.9 |
| 'Florida Sweetheart' | 3.3 | 3.1 | 2.8 |
| | 2008 | | |
| Cultivars | August | September | October |
| 'Passionista' | 4.8 a | 4.9 a | 4.4 a |
| 'Florida Red Ruffles' | 3.1 b | 2.7 b | 2.5 c |
| 'Florida Sweetheart' | 3.3 b | 3.3 b | 3.5 b |
| | 2009 | | |
| Cultivars | August | September | October |
| 'Passionista' | 4.0 a | 4.5[NS] | 4.3 a |
| 'Florida Red Ruffles' | 3.2 b | 3.7 | 3.5 b |
| 'Florida Sweetheart' | 4.7 a | 4.5 | 3.3 b |

[Z]Plants were rated on a scale of 1 to 5, with 1 being very poor, 3 fair and acceptable, and 5 being excellent in plant vigor, fullness, and color display, on 27 July, 28 August, and 15 September 2007; 16 August, 1 September, and 1 October 2008; and 12 August, 15 September, and 8 October 2009.
Mean values with the same letters within columns are not significantly different at $P \leq 0.05$.
NS: Not significantly different at $P \leq 0.05$.

As shown in Table 3, plant performance ratings of 'Passionista' ranged from 2.9 to 4.9 in nine evaluations over three growing seasons from 2007 to 2009. There were not significant differences between 'Passionista' and 'Florida Red Ruffles' or 'Florida Sweetheart' in plant performance rating in the 2007 growing season. The plant performance ratings of 'Passionista' were significantly higher than the ratings of 'Florida Red Ruffles' or 'Florida Sweetheart' in four or five out of the six evaluations in the 2008 and the 2009 growing seasons.

Table 4 shows the leaf sunburn tolerance of 'Passionista' with 'Florida Sweetheart' and 'Florida Red Ruffles' when tuber pieces were planted in ground beds and plants were grown in full sun in 2007, 2008 and 2009. Values presented are means of three replications in each year.

Leaf sun burn tolerance was evaluated on a scale of 1 to 5, with 1 being very susceptible to sun burns (leaves having numerous sun-damaged areas or holes) and 5 being resistant to sunburn (no visible sun-damaged areas). A total of nine evaluations were conducted for plant performance over three growing seasons in July, August, and September 2007, August, September, and October 2008, and August, September, and October 2009.

TABLE 4

| | 2007 | | |
|---|---|---|---|
| Cultivars | July | August | September |
| 'Passionista' | 3.6[Z, NS] | 2.9 b[y] | 3.0[NS] |
| 'Florida Red Ruffles' | 3.6 | 4.3 a | 4.0 |
| 'Florida Sweetheart' | 3.5 | 4.3 a | 3.8 |

TABLE 4-continued

| Cultivars | 2008 August | 2008 September | 2008 October |
|---|---|---|---|
| 'Passionista' | 4.8 a | 4.7 a | 1.8 b |
| 'Florida Red Ruffles' | 3.9 b | 2.3 b | 3.0 a |
| 'Florida Sweetheart' | 3.3 b | 3.2 b | 3.5 a |

| Cultivars | 2009 August | 2009 September | 2009 October |
|---|---|---|---|
| 'Passionista' | 5.0[NS] | 4.8[NS] | 4.7 a |
| 'Florida Red Ruffles' | 5.0 | 5.0 | 4.7 a |
| 'Florida Sweetheart' | 4.7 | 4.5 | 3.3 b |

[Z]Plant sunburn tolerance was rated on a scale of 1 to 5, with 1 being very poor, 3 fair and acceptable, and 5 being excellent without showing any signs of leaf burns or holes caused by sunburn on leaf surfaces, on 27 July, 28 August, and 15 September 2007; 16 August, 1 September, and 1 October 2008; and 12 August, 15 September, and 8 October 2009.
[Y]Mean values with the same letters within columns are not significantly different at $P \leq 0.05$. NS: Not significantly different at $P \leq 0.05$.

As shown in Table 4, the sunburn tolerance ratings of 'Passionista' were between 1.8 and 5.0. Plants of 'Passionista' showed less sunburn tolerance than 'Florida Red Ruffles' and 'Florida Sweetheart' in two evaluations. Strong sunlight frequently bleached out the pink color on the leaves of 'Passionista'.

The suitability of 'Passionista' for pot plant production was evaluated by forcing tubers in 11.4-cm containers in spring 2008. Intact No.1-sized tubers (>3.8 cm and <6.4 cm in diameter) were planted in a peat/vermiculite mix (VerGro Container Mix A, Verlite, Tampa, Fla.) on 17 Apr. 2008. The study was conducted in a greenhouse with 45% light exclusion. Average daily temperatures in the greenhouse ranged from a low of 16° C. at night to 29° C. during the day during the experiment. Potted plants were arranged on metal benches in the greenhouse in a randomized complete block design with eight replications. Plant height, plant width, number of leaves, and foliar characteristics were recorded on 12 Jun. 2008, 8 weeks after planting. Quality of the potted *Caladium* plants was rated on a scale of 1 to 5, 1=very poor, few leaves, totally unacceptable as potted plants, and 5=very attractive, with many bright, colorful leaves, a full plant, a symmetrical shape, and an appropriate height.

Table 5 shows a comparison of number of days to sprout, plant height, plant width, leaf number, leaf length, leaf width, and quality rating of 'Passionista' with 'Florida Sweetheart' and 'Florida Red Ruffles'.

TABLE 5

| Cultivars | Days to sprout[Z] (no.) | Plant height (cm) | Plant width (cm) | Leaves (no.) | Leaf length (cm) | Leaf width (cm) | Quality rating |
|---|---|---|---|---|---|---|---|
| Passionista' | 33.5[NS] | 22.9 a | 45.1 a | 20.4[NS] | 22.1 a | 12.1 b | 3.8[NS] |
| 'Florida Red Ruffles' | 35.3 | 18.3 b | 35.8 b | 19.1 | 17.9 b | 12.3 b | 3.7 |
| 'Florida Sweetheart' | 35.3 | 16.0 b | 33.5 b | 19.0 | 19.2 b | 14.6 a | 3.9 |

[Z]Number of days from planting to the first unfurled leaf.
[Y]Mean values within columns that share the same letters are not significantly different at $P < 0.05$. NS: Not significantly different at $P < 0.05$.

As shown in Table 5, intact No.1-sized tubers of 'Passionista' sprouted 33.5 days after planting, similar to the tubers of 'Florida Red Ruffles' and 'Florida Sweetheart'. Pot-grown plants of 'Passionista' had an average height of 22.9 cm and width of 45.1 cm, 4.6 to 6.9 cm taller and 9.3 to 11.6 cm wider than plants of 'Florida Red Ruffles' and 'Florida Sweetheart', respectively. Plants of 'Passionista' produced similar numbers of leaves as plants of 'Florida Red Ruffles' and 'Florida Sweetheart'. Leaves of 'Passionista' had an average size of 22.1 cm in length and 12.1 cm in width. Leaves of 'Passionista' were 4.2 cm longer than the leaves of 'Florida Red Ruffles' and 2.9 cm longer but 2.5 cm narrower than the leaves of 'Florida Sweetheart'. Intact tubers of 'Passionista' produced quality pot plants in 8 weeks, with an average plant quality rating of 3.8, similar to that of 'Florida Red Ruffles' and 'Florida Sweetheart'.

What is claimed:

1. A new and distinct cultivar of *Caladium* plant named 'Passionista', as illustrated and described herein.

* * * * *